United States Patent [19]

Schneider

[11] 4,168,282
[45] Sep. 18, 1979

[54] PROCESS FOR THE PREPARATION OF SUBSTITUTED NORBORNENE DERIVATIVES

[75] Inventor: Wolfgang Schneider, Broadview Heights, Ohio

[73] Assignee: The B. F. Goodrich Company, Akron, Ohio

[21] Appl. No.: 906,178

[22] Filed: May 15, 1978

[51] Int. Cl.$^2$ .............................................. C07C 3/04
[52] U.S. Cl. ...................................... 585/361; 585/22
[58] Field of Search ..................... 260/666 PY, 666 D

[56] References Cited

U.S. PATENT DOCUMENTS

| | | | |
|---|---|---|---|
| 2,524,086 | 10/1950 | Schmerling | 260/668 R |
| 2,991,308 | 4/1961 | Cohen | 260/666 PY |
| 3,007,977 | 11/1961 | Hill et al. | 260/666 PY |
| 3,427,360 | 2/1969 | Makowski | 260/666 PY |
| 3,766,283 | 10/1973 | Lorette | 260/666 PY |

OTHER PUBLICATIONS

Chem. Ab. 50:11257g; 58:8925e.

*Primary Examiner*—Veronica O'Keefe
*Attorney, Agent, or Firm*—Nestor W. Shust

[57] ABSTRACT

Mono or dialkyl substituted norbornenes or cyclic norbornene derivatives are prepared by condensing an appropriate olefin or an ethylenically unsaturated alicyclic compound with dicyclopentadiene or cyclopentadiene at an elevated temperature and pressure in the presence of a chlorinated hydrocarbon solvent.

11 Claims, No Drawings

PROCESS FOR THE PREPARATION OF SUBSTITUTED NORBORNENE DERIVATIVES

BACKGROUND OF THE INVENTION

Preparation of norbornene or monoalkyl substituted norbornenes is well known in the art. Normally an α-olefin is condensed with cyclopentadiene or dicyclopentadiene at elevated temperatures and pressures. However, the basic process is unsatisfactory because considerable amounts of resinous materials are formed which slowly build up in the reactor and associated equipment. The internally unsaturated olefins are somewhat less reactive than α-olefins which require even higher reaction temperatures and longer residence time which causes even greater buildup of thermal polymers than when α-olefins are employed. To combat the polymer buildup prior art has suggested carrying out the reaction in the presence of a large excess of olefin (U.S. Pat. No. 2,991,308), or in the presence of hydrocarbon solvent (U.S. Pat. No. 3,766,283). Although hydrocarbon solvents are helpful in reducing the polymer buildup when norbornene or monoalkyl norbornenes are prepared, there is still a considerable polymer buildup which makes the process not very practical commercially. However, in the preparation of dialkylnorbornenes or cyclic norbornene derivatives hydrocarbon solvents have little or no effect on the buildup of polymers.

DETAILED DESCRIPTION

This invention is directed to the process for preparing substituted norbornene derivatives of the general formula

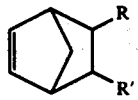
(I)

wherein R and R' are independently alkyl or alkylene groups of 1 to 20 carbon atoms, provided that the total number of carbon atoms for R and R' is not greater than 20; preferably R and R' are 1 to 10 and most preferably 1 or 2 carbon atoms; or R and R' together with the ring carbons to which they are bonded form one or more, and preferably one or two, saturated or unsaturated rings of 6 to 16 carbon atoms, and more preferably 6 to 10 carbon atoms, or one of R and R' is hydrogen while the other is as defined above; said process comprising reacting cyclopentadiene or dicyclopentadiene with an olefin or cycloolefin at a temperature between 100° and 300° C., at a pressure sufficient to maintain the reaction in liquid phase and in the presence of a chlorinated or brominated hydrocarbon solvent.

Depending on the olefin employed the resulting norbornene derivative will be a monoalkyl, a monoalkylene, a dialkyl, a monoalkyl-monoalkylene, a dialkylene or a cyclic derivative. More specifically, if the olefin employed is an α-monoolefin then a monoalkyl substituted norbornene is obtained. The useful α-olefins have 1 to 22 carbon atoms, preferably from practical point of view 1 to 12 and especially 1 to 4 carbon atoms. Typical examples of α-olefins are ethylene, propylene, butene, pentene, hexene, octene, decene, dodecene, tetradecene, hexadecene, octadecene and the like. If a diolefin, which has at least one unsaturation on the α-carbon, is employed then a monoalkylene substituted norbornene is obtained. Typical examples of diolefins, which can have up to 22 carbon atoms, preferably up to 12 carbon atoms, are butadiene-1,2, butadiene-1,3, pentadiene-1,2, pentadiene-1,3, pentadiene-1,4, hexadiene-1,2, hexadiene-1,3, hexadiene-1,4, and the various isomers of heptadiene, octadiene, deca-diene, dodecadiene, tetradecadiene, hexadecadiene, octadeca-diene and the like.

When an internal olefin, that is, an olefin which contains unsaturation on other than α-carbons, is employed, the resulting product is a dialkyl substituted norbornene of the formula

(II)

wherein $R_1$ and $R_2$ are independently alkyl groups of 1 to 20 carbon atoms, provided that the total number of carbon atoms for $R_1$ and $R_2$ is not greater than 20. Preferably $R_1$ and $R_2$ are independently alkyl of 1 to 10 and most preferably 1 or 2 carbon atoms. The internal olefins useful in preparing such dialkyl norbornenes are, for example, butene-2, pentene-2, hexene-2, hexene-3, heptene-2, heptene-3, octene-2, octene-3, octene-4, nonene-2, 3 or 4, decene-2, 3, 4 or 5, undecene-2, 3, 4, or 5, and dodecene-2, 3, 4, 5 or 6. Higher internal olefins having up to 18 carbon atoms can also be employed but for practical reasons they are not preferred.

If an olefin containing two internal ethylenic unsaturations is condensed with a cyclopentadiene, one of the substituents $R_1$ and $R_2$ in formula II above will be alkyl and the other alkenyl while both will be alkenyl if the internal olefin has three or more ethylenic unsaturations. Illustrative examples of internal olefins containing two or more ethylenic unsaturations are hexadiene-2,4, heptadiene-2,4 or 2,5 or 3,5, octadiene-2,4 or 2,5 or 2,6 or 3,5 or 3,6, and the various isomers of decadiene, dodecadiene, tetradecadiene, hexadecadiene, octadecadiene and the like, octatriene-2,4,5, decatriene-2,4,5 or 2,4,6 or 3,5,7 and the like and various isomers of dodecatriene, tetra, hexa and octadecatrienes, decatetraene-2,4,6,8 and other tetraene isomers.

If, on the other hand, an ethylenically unsaturated alicyclic compound is condensed with cyclopentadiene or dicyclopentadiene, the resulting product is a cyclic norbornene derivative of the formula

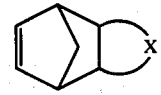

wherein X is an alkylene or an alkenylene chain having 4 to 16 carbon atoms and preferably 4 to 10 carbon atoms. The cyclic ethylenically unsaturated compounds that can be employed in preparing cyclic norbornene derivatives can have one to four ethylenic unsaturations. If a monoethylenically unsaturated cyclic compound is employed, the resulting cyclic derivative would have a structure

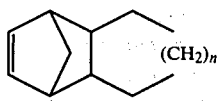

where n is from 2 to 14. If the cyclic compound has two or more ethylenic unsaturations, the resulting cyclic norbornene derivative will have one or more ethylenic unsaturations. Thus when the cyclic olefin has three or four ethylenic unsaturations a novel class of cyclic norbornene derivatives is obtained which can be represented by the formula

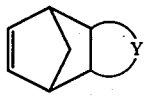

wherein Y is an alkenylene group of 8 to 20 carbon atoms containing two or three ethylenic unsaturations.

Illustrative examples of ethylenically unsaturated alicyclic compounds are cyclobutene, cyclopentene, cyclohexene, cycloheptene, cyclooctene, cyclodecene, cyclododecene, cyclotridecene, cyclotetradecene, cyclohexadecene, cyclooctadecene, cyclohexadiene-1,3, cyclohexadiene-1,4 cyclooctadiene-1,3 cyclooctadiene-1,4 cyclooctadiene-1,5 and various isomers of cyclodecadiene, cyclododecadiene, cyclotetradecadiene, cyclohexadecadiene and cyclooctadecadiene, cyclooctatriene-1,3,5, cyclooctatriene-1,3,6, cyclooctatriene-1,3,7 and other isomers, and the various isomers of cyclododecatriene, cyclotetradecatriene, cyclohexadecatriene and cyclooctadecatriene as well as the various isomers of cyclodecatetraene, cyclododecatetraene, cyclohexadecatetraene and cyclooctadecatetraene, cyclooctatetraene-1,3,5,7, cyclodecatetraene-1,3,5,7, cyclodecatetraene-1,3,5,8 and all other isomers of cyclodecatetraene as well as various isomers of cyclododecatetraene, cyclotetradecatetraene, cyclohexadecatetraene and cyclooctadecatetraene.

The various cyclic unsaturated compounds are known in the art and can be made by various methods, including the oligomerization of butadiene.

The process of this invention can be carried out at a temperature between 100° and 300° C. but preferably between 240° C. and 280° C. At temperatures below 200° C. selectivity and conversion was progressively lower and therefore the residence time had to be increased. At temperatures above 280° C. the undesirable polymer buildup started to increase which eventually caused the reactor and other equipment to plug up. Selectivity, conversion and yield also varied with the residence time. Although residence time may be from 0.5 to 2.5 hours, from the standpoint of better selectivity, conversion and yield it is preferable that the residence time be held between 1 hour and 2.5 hours and more preferably between 1.25 hours and 2 hours.

The molar ratios of olefin to cyclopentadiene can be from 1:1 to 10:1. Generally, as the ratio is increased, selectivity, conversion and yield also increase, especially at lower temperatures, but at ratios higher than 5:1 conversion and yield decrease somewhat while selectivity continues to increase. Therefore the preferred ratio is from 2:1 to 5:1.

The most important and critical feature of the process of this invention is the use of a chlorinated or brominated solvent as the reaction medium. The chlorinated or brominated hydrocarbon solvents may be aliphatic or aromatic and may be halogenated to various degrees. As noted, both chlorinated and brominated solvents can be employed equally successfully, but for economic and practical reasons chlorinated solvents are preferred.

Illustrative examples of chlorinated hydrocarbon solvents are chloroform, carbontetrachloride, dichloroethane, trichloroethane(methylchloroform), tetrachloroethane, chloropropane, dichloropropane, trichloropropane, pentachloropropane, chlorobutane, dichlorobutane, trichlorobutane, pentachlorobutane, heptachlorobutane, dichlorobenzene, dichlorotoluene, trichlorobenzene and the like. In addition to minimizing the buildup of undesirable polymers, when the process is carried out in a chlorinated solvent a homogeneous reaction product is obtained and cyclopentadiene oligomer (e.g. dimer, trimer, tetramer) and polymer can be directly recycled as a liquid feed stock into the reactor without the need of first cracking the liquid/solid cyclopentadiene oligomer or polymer in a separate pyrolysis unit.

The ratio of a chlorinated solvent to butene can be in the range from 0.5:1 to 5:1 and preferably from 0.8:1 to 3:1.

The reaction is carried out at a pressure sufficient to maintain a liquid phase. When higher boiling olefins are employed the reaction could be carried out even at atmospheric pressure. However, since the process is carried out at a relatively high temperature, it is preferable to use also elevated pressures between 50 and 2,500 psi. The actual pressure employed depends on the olefin used. The higher molecular weight olefins would be reacted at a pressure in the lower range while the lower olefins would be reacted at a pressure in the higher range. For example cyclopentadiene would be reacted at a pressure of 50-200 psi, butene-2 at a pressure of 1400-1800 psi while ethylene at a pressure of 2000-2500 psi.

The above described process yields various stereoisomers of dialkyl substituted norbornene, that is, cis endo, cis-exo, trans-endo and exo forms. Below 180° C. the endo form was primarily produced while above 180° C. the exo isomer was also produced. Although the various isomers could be isolated, for practical reasons the mixture is most useful commercially. When cis and trans butene-2 is reacted with cyclopentadiene above 260° C., the product obtained predominates in the trans isomer. The preferential formation of trans dialkyl norbornene above 260° C. remained regardless of the residence time for the ratio of butene-2 to cyclopentadiene employed.

From the above description of the process of this invention it is evident that there are many variables in the process, that is, temperature, pressure, and the various ratios of the two reactants and of the chlorinated solvent to the internally unsaturated compound. The various conditions and ratios can be adjusted in such a way as to yield the desired product at the desired conversion and yield. Although the process of this invention can be operated as a batch process, the reproducibility is not very good. Therefore it is preferable to carry out this process in a continuous manner. The Examples below further illustrate the present invention without introducing any limitations thereto.

BATCH PROCESS

A 1.7 liter autoclave was preheated to 260° C. and a solution of 2 moles of butene-2 and 1 mole of cyclopentadiene in two moles of methylchloroform (1,1,1-trichloroethane) was pumped into the autoclave in less than one-half hour and left to react for an additional two hours. During the reaction the temperature was maintained at about 240° C. At the end of the reaction period the crude reaction product was flash distilled to yield a partially purified product which contained at least 65% of the desired product and up to 35% of dicyclopentadiene.

CONTINUOUS PROCESS

The apparatus consisted of a tubular reactor consisting of a ⅜ inch O.D.×150 feet SS Tubing which was cold-rolled into loops. The coil was heated in an air oven to a temperature noted in the table. The reaction mixture containing 2 moles of an olefin or an ethylenically unsaturated alicyclic compound, 1 mole of cyclopentadiene and 2 moles of methylchloroform was fed into the reactor with a metering pump. The residence time was as noted in the table. The crude reaction product was then flash-distilled.

EXAMPLES 1-14

Following the procedure of the continuous process, 4 moles of cis, trans, butene-2 was reacted with 1 mole of dicyclopentadiene in 4 moles of methyl chloroform under the various conditions given in Table I below to yield cis 5,6-dimethylnorbornene (endo and exo form) (cDMNB) and trans 5,6-dimethylnorbornene-2 (tDMNB) also reported in Table I. Conversion of dicyclopentadiene (DCPD) at various temperatures at a given residence time is noted.

TABLE I

| Ex. No. | Temp. ° C. | Residence Time (hr) | Conversion DCPD | Selectivities | |
|---|---|---|---|---|---|
| | | | | cDMNB | t-DMNB |
| 1 | 200 | 0.5 | 3 | 31 | 8 |
| 2 | 220 | 0.5 | 11 | 31 | 21 |
| 3 | 240 | 0.5 | 18 | 31 | 21 |
| 4 | 260 | 0.5 | 33 | 31 | 26 |
| 5 | 280 | 0.5 | 43 | 31 | 35 |
| 6 | 300 | 0.5 | 46 | 25 | 37 |
| 7 | 200 | 1.3 | 7 | 28 | 23 |
| 8 | 220 | 1.3 | 18 | 31 | 20 |
| 9 | 240 | 1.3 | 36 | 32 | 24 |
| 10 | 260 | 1.3 | 53 | 33 | 30 |
| 11 | 280 | 1.3 | 56 | 27 | 40 |
| 12 | 200 | 2.3 | 8 | 30 | 19 |
| 13 | 220 | 2.3 | 20 | 31 | 21 |
| 14 | 240 | 2.3 | 48 | 21 | 26 |

EXAMPLES 15-27

Cyclopentene (CPE) and cyclopentadiene (CPD) are reacted in a continuous process at the indicated mole ratios in methylchloroform (same number of moles as CPE) with residence times and at temperatures noted in Table II to yield dihydrodicyclopentadiene.

TABLE II

| Ex. No. | Mole Ratio CPE/CPD | Residence Time (hrs) | Temperature ° C. |
|---|---|---|---|
| 15 | 2 | 0.6 | 200 |
| 16 | 2 | 0.6 | 240 |
| 17 | 2 | 0.6 | 280 |
| 18 | 2 | 3.0 | 180 |
| 19 | 2 | 3.0 | 240 |
| 20 | 5 | 0.3 | 220 |
| 21 | 5 | 0.3 | 260 |
| 22 | 5 | 0.6 | 200 |
| 23 | 5 | 0.6 | 240 |
| 24 | 5 | 0.6 | 280 |
| 25 | 5 | 1.1 | 200 |
| 26 | 5 | 1.1 | 240 |
| 27 | 5 | 1.1 | 280 |

Conversion and selectivity are highest when the reaction is carried out between 220° and 280° C. at any mole ratio of CPE/CPD and at any residence time. However conversion is lowest at 0.3 hr. residence time.

EXAMPLES 28-44

Butene-2 (B-2) and cyclopentadiene (CPD) are reacted in a continuous process at the indicated mole ratios in methylchloroform (same number of moles as B-2) with residence times and at temperatures indicated in Table III to yield cis and trans 5,6-dimethylnorbornene-2.

TABLE III

| Ex. No. | Mole Ratio B-2/CPD | Residence Time (hrs) | Temperature ° C. |
|---|---|---|---|
| 8 | 2 | 0.5 | 200 |
| 29 | 2 | 0.5 | 240 |
| 30 | 2 | 0.5 | 280 |
| 31 | 2 | 1.3 | 200 |
| 32 | 2 | 1.3 | 240 |
| 33 | 5 | 0.5 | 200 |
| 34 | 5 | 0.5 | 240 |
| 35 | 5 | 0.5 | 280 |
| 36 | 5 | 1.3 | 200 |
| 37 | 5 | 1.3 | 240 |
| 38 | 5 | 1.3 | 280 |
| 39 | 10 | 1.3 | 200 |
| 40 | 10 | 1.3 | 240 |
| 41 | 10 | 1.3 | 300 |
| 42 | 10 | 2.3 | 200 |
| 43 | 10 | 2.3 | 240 |
| 44 | 10 | 2.3 | 300 |

EXAMPLE 45

Following the batch procedure, 66 g. (0.5 mole) of dicyclopentadiene is reacted with 110.2 g. (1.0 mole) of cyclooctene in 300 g. of 0-dichlorobenzene. The reaction is carried out for 3 hours at 220° C. yielding 2,3-hexamethylenenorbornene-5.

EXAMPLE 46

Following the batch procedure, 162.3 g (1 mole) of 1,5,9-cyclododecatriene and 66.0 g. (0.5 mole) of dicyclopentadiene in 100 g. of methylchloroform are reacted for 4 hours at 200° C. to yield a high yield of tricyclo [12.2.1.0$^{2,13}$] heptadeca-5,9,15-triene.

EXAMPLE 47

82 g. (1 mole) of cyclohexene and 66 g. (0.5 mole) of dicyclopentadiene are reacted according to the batch procedure in 300 g. of chloroform. The reaction is carried out for 5 hours at 220° C. to produce a moderate yield of tricyclo [6.2.1.0$^{2,7}$] undec-9-ene.

EXAMPLE 48

Following the batch procedure, 112 g. (2 moles) of butene-1 is reacted with 132 g. (1 mole) of dicyclopentadiene in 400 g. of methylchloroform. The reaction is carried out for one hour at 250° C. to produce a good yield of ethylnorbornene-5.

EXAMPLE 49

Following the batch procedure, 108.6 g. (1 mole) of pentalene and 66 g. (0.5 mole) of dicyclopentadiene in 250 g. of 1,1-dichloroethane are reacted for 3 hours at 220° C. to yield a good yield of tetracyclo [8.2.1.0$^{9,20}$7,$^3$] tridecene-11.

What is claimed is:

1. A process for preparing substituted norbornene derivatives of the formula

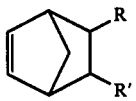

wherein R and R' are independently alkyl or alkylene groups of 1 to 20 carbon atoms provided that the total number of carbon atoms for R and R' is not greater than 20, or R and R' together with the ring carbons to which they are bonded form one or more saturated or unsaturated rings of 6 to 16 carbon atoms, or one of R and R' is hydrogen, said process comprising reacting cyclopentadiene or dicyclopentadiene with an olefin or a cycloolefin at a temperature between 100° and 300° C., at a pressure sufficient to maintain the reaction in liquid phase which is between 50 and 2500 psi and in the presence of a chlorinated or a brominated hydrocarbon solvent.

2. A process of claim 1 wherein the temperature is between 240° and 280° C. and the solvent is a chlorinated hydrocarbon.

3. A process of claim 2 for preparing a norbornene derivative wherein one of R and R' is hydrogen and the reaction is carried out at a pressure of between 1400 and 2500 psi.

4. A process of claim 2 for preparing a norbornene derivative wherein R and R' are independently alkyl groups.

5. A process of claim 2 for preparing a norbornene derivative wherein one of R and R' is alkyl and the other alkenyl.

6. A process of claim 2 for preparing a norbornene derivative wherein R and R' are independently alkenyl groups.

7. A process of claim 2 for preparing a norbornene derivative wherein R and R' together with the ring carbons to which they are bonded form a saturated ring of 6 to 10 carbon atoms.

8. A process of claim 2 for preparing a norbornene derivative wherein R and R' together with the ring carbons to which they are bonded form an unsaturated ring of 6 to 10 carbon atoms.

9. A process of claim 3 wherein the other of R and R' is alkyl of 1 to 4 carbon atoms.

10. A process of claim 4 wherein said alkyl groups have 1 to 4 carbon atoms.

11. A process of claim 7 wherein said saturated ring has 6 carbon atoms.

* * * * *